(12) United States Patent
Rudy, Jr. et al.

(10) Patent No.: US 6,634,359 B1
(45) Date of Patent: Oct. 21, 2003

(54) TRACHEAL TUBE HOLDING DEVICE

(75) Inventors: Ronald M. Rudy, Jr., Boynton Beach, FL (US); Freddy T. Lee, Boynton Beach, FL (US); Thomas Murphy, Boynton Beach, FL (US)

(73) Assignee: Insight Medical Design, Inc., Boynton Beach, FL (US)

( * ) Notice: Subject to any disclaimer, the term of this patent is extended or adjusted under 35 U.S.C. 154(b) by 15 days.

(21) Appl. No.: 09/710,960

(22) Filed: Nov. 14, 2000

(51) Int. Cl.$^7$ ............................................ A61M 16/00
(52) U.S. Cl. .............................. 128/207.14; 128/202.27
(58) Field of Search ......... 128/200.26, 207.14–207.18, 128/911, 912, DIG. 26, 202.27; 604/178, 179

(56) References Cited

U.S. PATENT DOCUMENTS

| | | | | |
|---|---|---|---|---|
| 2,908,269 A | * | 10/1959 | Cheng .......................... 128/12 |
| 3,760,811 A | * | 9/1973 | Andrew ................. 128/207.17 |
| 4,249,529 A | * | 2/1981 | Nestor et al. .......... 128/207.17 |
| 4,360,025 A | | 11/1982 | Edwards .................... 604/180 |
| 4,520,813 A | | 6/1985 | Young ................. 128/207.17 Z |
| 4,683,882 A | | 8/1987 | Laird ..................... 128/207.17 |
| 4,699,616 A | | 10/1987 | Nowak et al. ............... 604/180 |
| 4,774,944 A | * | 10/1988 | Mischinski ............ 128/207.17 |
| 4,832,019 A | * | 5/1989 | Weinstein et al. ..... 128/207.17 |
| 4,906,234 A | * | 3/1990 | Voychehovski ............... 604/79 |
| 4,932,943 A | | 6/1990 | Nowak ........................ 604/180 |
| 4,986,815 A | | 1/1991 | Schneider .................... 604/180 |
| 5,026,352 A | * | 6/1991 | Anderson .................... 604/178 |
| 5,069,206 A | * | 12/1991 | Crosbie .................. 128/207.17 |
| 5,076,269 A | * | 12/1991 | Austin .................... 128/207.17 |
| 5,215,531 A | | 6/1993 | Maxson et al. ............. 604/180 |
| 5,295,480 A | | 3/1994 | Zemo ..................... 128/207.17 |
| 5,320,097 A | * | 6/1994 | Clemens et al. ....... 128/207.17 |
| 5,345,931 A | * | 9/1994 | Battaglia, Jr. .......... 128/207.17 |
| 5,402,776 A | | 4/1995 | Islava ..................... 128/207.17 |
| 5,437,273 A | * | 8/1995 | Bates et al. ............. 128/207.17 |
| 5,551,421 A | * | 9/1996 | Noureldin et al. ..... 128/207.17 |
| 5,653,232 A | * | 8/1997 | Rogers et al. .......... 128/207.17 |
| 5,803,079 A | * | 9/1998 | Rogers et al. .......... 128/207.14 |
| 5,806,516 A | * | 9/1998 | Beattie .................. 128/207.17 |
| 5,894,840 A | * | 4/1999 | King ..................... 128/200.26 |
| 5,934,276 A | * | 8/1999 | Fabro et al. ........... 128/207.17 |
| 6,009,872 A | * | 1/2000 | Delaplane et al. ..... 128/207.17 |
| 6,010,484 A | * | 1/2000 | McCormick et al. ....... 604/174 |
| 6,029,668 A | * | 2/2000 | Freed .................... 128/207.17 |
| 6,067,985 A | * | 5/2000 | Islava ..................... 128/207.17 |
| 6,408,850 B1 | * | 6/2002 | Sudge ................... 128/207.17 |

* cited by examiner

Primary Examiner—Aaron J. Lewis
Assistant Examiner—Teena Mitchell
(74) Attorney, Agent, or Firm—Roylance, Abrams, Berdo & Goodman, L.L.P.

(57) ABSTRACT

A tracheal tube holding and stabilizing device includes a support having an open slot for receiving a tracheal tube. A pivotally mounted jaw is coupled to the support to close the slot and clamp the tracheal tube in position. The support includes a flexible arm having ratcheting teeth for engaging complementing ratcheting teeth on an outer end of the jaw. The jaw includes an open slot on one side to receive the tracheal tube in the clamping position. In this manner, the tracheal tube is securely clamped in the slot of the support and the slot in the pivotable jaw.

37 Claims, 6 Drawing Sheets

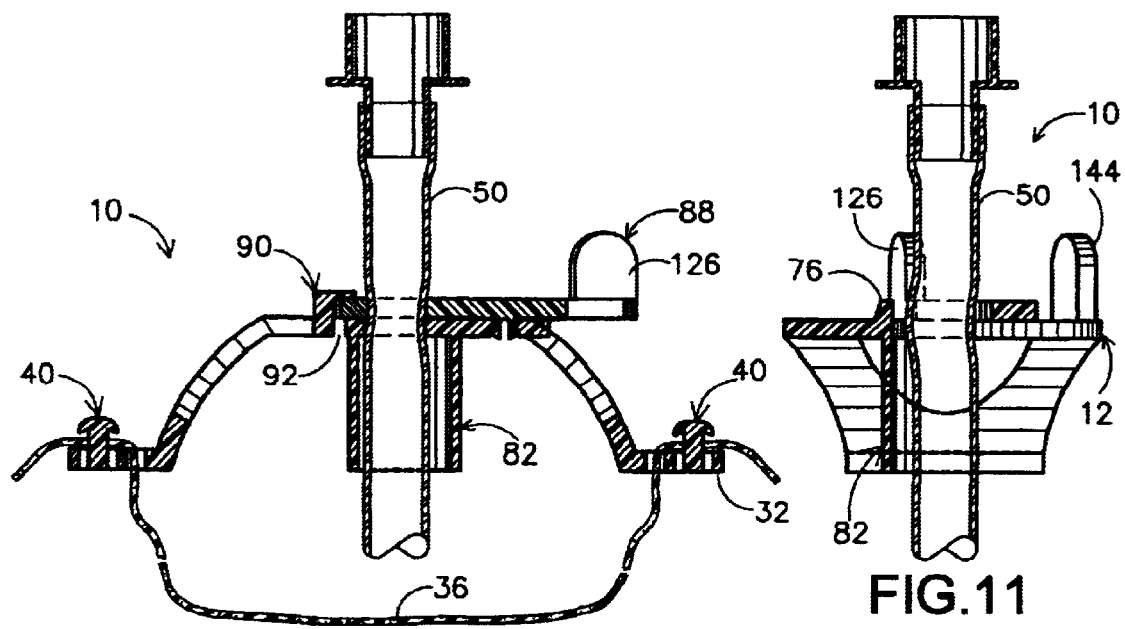
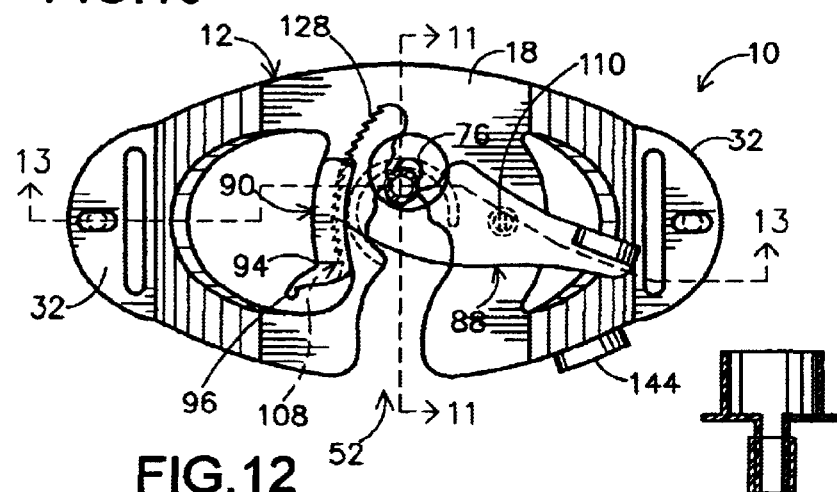
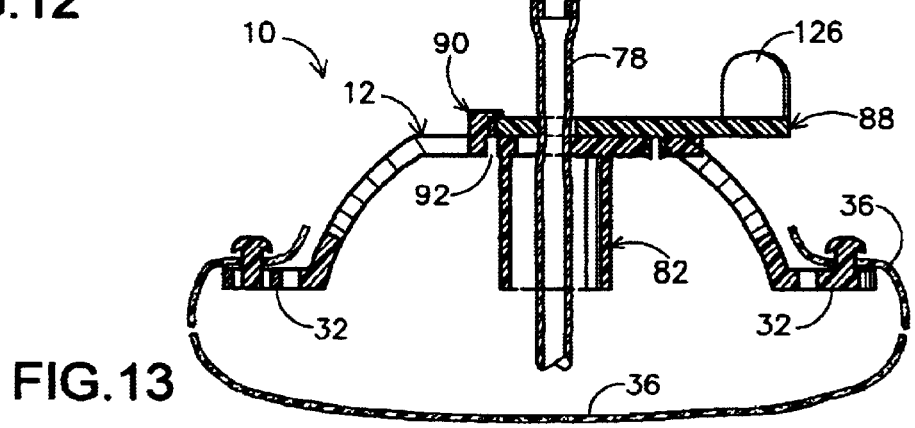

TRACHEAL TUBE HOLDING DEVICE

FIELD OF THE INVENTION

The present invention is directed to a device for holding and stabilizing a tracheal tube in the mouth of a patient. More particularly, the invention is directed to a device having a clamping assembly for stabilizing a tracheal tube.

BACKGROUND OF THE INVENTION

Tracheal tubes are commonly used for ventilating a patient during resuscitation, administration of anesthesia, and other. emergency medical procedures The effective use of the tracheal tube requires that the tracheal tube be properly position in the trachea. The tracheal tube must be positioned at the correct level in the trachea to provide proper ventilation of the patient. Positioning the tracheal tube to an insufficient depth in the trachea can prevent a proper seal in the throat and increase the likelihood of the tracheal tube being pulled or dislodged from the throat. Extending the tracheal tube too far into the trachea can result in irritation and non-uniform ventilation.

A common practice of securing a tracheal tube in place is to simply tape the tube with a suitable adhesive tape. This method is uncomfortable to the patient and increases the difficulty of removing the tube. Recently, the use of tape to secure the tracheal tube has been discouraged and prohibited in many instances. To overcome the disadvantages of taping the tracheal tube in place, numerous devices have been proposed for stabilizing the tracheal tube. These devices typically have a head band encircling the patient's head or neck to secure the device in place.

One example of an endotracheal tube stabilizer is disclosed in U.S. Pat. No. 5,806,516 to Beattie. This device includes a frame having a tube channel for receiving an endotracheal tube. Straps are provided for securing the frame to the head with the frame bridging the mouth. A movable clamp slides on an arcuate track for clamping the tube in the channel of the frame. The clamp has a foot moving in an arcuate path from an open position to an operative position blocking the opening of the channel. A ratchet is provided on the arcuate track of the clamp to secure the clamp in the locking position.

An example of a nasogastric tube holding device is disclosed in U.S. Pat. No. 4,932,943 to Nowak. This device includes an adhesive pad and a pair of independent clamping jaws pivotally supported on one end of the pad. The jaws include an adjustable latching device for releasably holding the tube in place.

A number of other devices for holding a tracheal tube include a band or a pair of clamping jaws to clamp the tube in place. Examples of this type of device are disclosed in U.S. Pat. Nos. 5,076,269 to Austin, 5,069,206 to Crosbie, 5,295,480 to Zemo and 5,320,097 to Clemens et al.

Although generally effective for their intended purpose, the prior devices have experienced limited success in the marketplace. Accordingly, there is a continuing need in the industry for an improved endotracheal tube holding device.

SUMMARY OF THE INVENTION

The present invention is directed to a device for holding a tracheal tube in the mouth of a patient. The invention is further directed to a device for clamping and stabilizing a tracheal tube and supporting the tracheal tube in a selected position in the patient's mouth.

Accordingly, a primary object of the invention is to provide a tracheal tube holding device having a clamping assembly capable of securely clamping and stabilizing a tracheal tube.

Another object of the invention is to provide a tracheal tube holding device that is simple to operate and able to securely clamp the tracheal tube in place.

Another object of the invention is to provide a tracheal tube holding device that is able to effectively stabilize and accommodate different sizes of tracheal tubes.

Still another object of the invention is to provide a tracheal tube holding device having a clamping assembly that can be operated with one hand.

A further object of the invention is to provide a tracheal tube holding device having a clamping assembly and an adjustable headband for securing the device on the patient.

Another object of the invention is to provide a tracheal tube holding device having a latching assembly with a movable jaw that is able to move in and out of engagement with the tracheal tube.

A further object of the invention is to provide a tracheal tube holding device having a clamping assembly that is able to stabilize the tracheal tube without twisting or distorting the tracheal tube.

Another object of the invention is to provide a tracheal tube holding device having a latching assembly with a ratcheting jaw to clamp the tracheal tube to the device.

A further object of the invention is to provide a tracheal tube holding device having an opening for receiving a tracheal tube where the opening has a first recessed area for receiving a tracheal tube of a first size and a second recessed area for receiving a tracheal tube of a second size.

A further object of the invention is to provide a tracheal tube holding device having a ratcheting jaw and a flexible arm with ratcheting teeth for engaging the jaw where the flexible arm can be flexed away from the jaw to release the ratcheting teeth and allow the jaw to open.

Another object of the invention is to provide a tracheal tube holding device having a support with a first latching member at a first end of the support and a jaw pivotally connected to the support and having a second latching member for latching with the first latching member.

A further object of the invention is to provide a tracheal tube holding device having a support and a jaw coupled together by a living hinge, where the support and the jaw each include an adjustable latching assembly for latching the jaw in a selected position with respect to the support.

The objects of the invention are basically attained by providing a tracheal tube holding device for stabilizing a tracheal tube in the mouth of a patient. The device comprises a frame dimensioned to fit over a patient's mouth and having an opening extending transversely through the frame and being dimensioned to receive a tracheal tube. A jaw pivotally coupled to the frame is pivotable about a pivot axis on the frame between an open position to a clamping position to clamp a tube in the opening of the frame. A releasable latching assembly latches the jaw in the clamping position.

The objects of the invention are also attained by providing a tracheal tube holding device for stabilizing a tracheal tube in the mouth of a patient. The device comprises a support dimensioned to fit over a patient's mouth. The support has a first end, a second end, and first and second sides extending between the first and second ends. The first side has an open slot defining an opening extending transversely through the support for receiving a tracheal tube. A jaw is pivotally coupled to the support. The jaw has a side with a slot therein complementing the slot in the frame. The jaw is pivotable between an open position and a clamping position to clamp a tracheal tube in the slot in the frame and the slot in the jaw. A releasable latching assembly latches the jaw in the clamping position.

The objects of the invention are further attained by providing a tracheal tube holding device holding a tracheal tube in the mouth of patient, comprising a support dimensioned to fit over a patient's mouth. The support has a first end, a second end and an opening extending transversely through the support for receiving a tracheal tube. The opening is located between the first and second ends. A jaw is coupled to the support and is pivotable about a pivot axis. The jaw is pivotable between an open position and a clamping position. The jaw has a first end with a first latching member. A second latching member is coupled to the first end of the support and is positioned to engage the first latching member of the jaw for latching the jaw in the clamping position.

The objects, advantages and other salient features of the invention will become apparent from the following detailed description of the invention and the annexed drawings, which form a part of this original disclosure.

BRIEF DESCRIPTION OF THE DRAWINGS

The following is a brief description of the drawings, in which:

FIG. 10 is a cross-sectional end view of the device of FIG. 6 taken along lines 10—10 of FIG. 6;

FIG. 11 is a cross-sectional side view of the device taken along line 11—11 of FIG. 6;

FIG. 12 is a top view of the device showing a small diameter tracheal tube clamped in the device;

FIG. 13 is a cross-sectional view of the device of FIG. 12 taken along line 13—13 of FIG. 12;

DETAILED DESCRIPTION OF THE INVENTION

Figure 1:
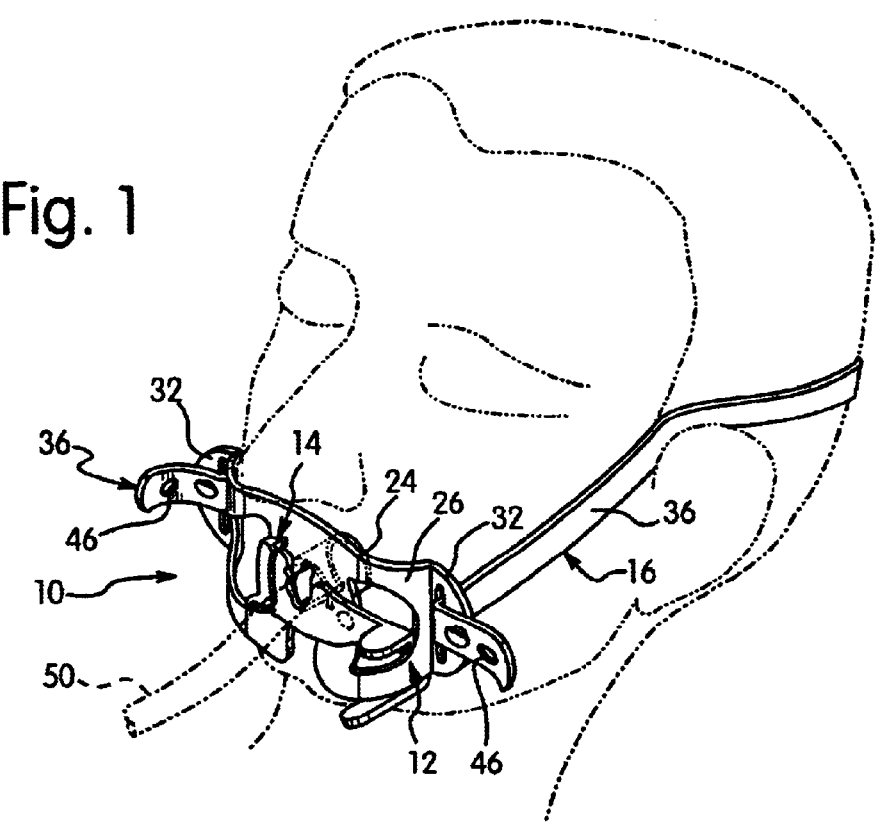
FIG. 1 is a perspective view of the tracheal tube holding device in a first preferred embodiment of the invention.

The present invention is directed to a device for holding and stabilizing a tracheal tube in the mouth and throat of a patient. More particularly, the invention is directed to a device for clamping a tracheal tube in a secure position to prevent the tube from moving within the patient's throat during ventilation of the patient.

Referring to the drawings, the tracheal tube holding device 10 includes a frame 12 forming a primary support. Frame 12 includes a clamping assembly 14 and an attaching member 16 for attaching device 10 to a patient. In preferred embodiments of the invention, device 10 is made of a lightweight plastic material that is sufficiently strong to stabilize a tracheal tube and hold the tracheal tube in a fixed position. Generally, the various components of device 10 are made by injection molding from suitable plastic materials such as, for example, polyethylene or polypropylene. The plastic material is sufficiently flexible to enhance the comfort to the patient and to improve the handling properties for the operator.

As shown in the drawings, frame 12 has a substantially planar central body portion 18. Central body portion 18 has a width sufficient to substantially cover the mouth of a patient. Central body portion 18 has a first longitudinal edge 20 and a second longitudinal edge 22 extending between side edges 24. Substantially arcuate shaped legs 26 are integrally formed with central body portion 18 along side edges 24. Arcuate shaped legs 26 have a shape and dimension to conform around a patient's mouth as shown in FIG. 1 to increase the comfort to the patient and to assist in seating the device against the mouth of the patient. In alternative embodiments, legs 26 can be flat and extend parallel to body portion 18.

Figure 2:
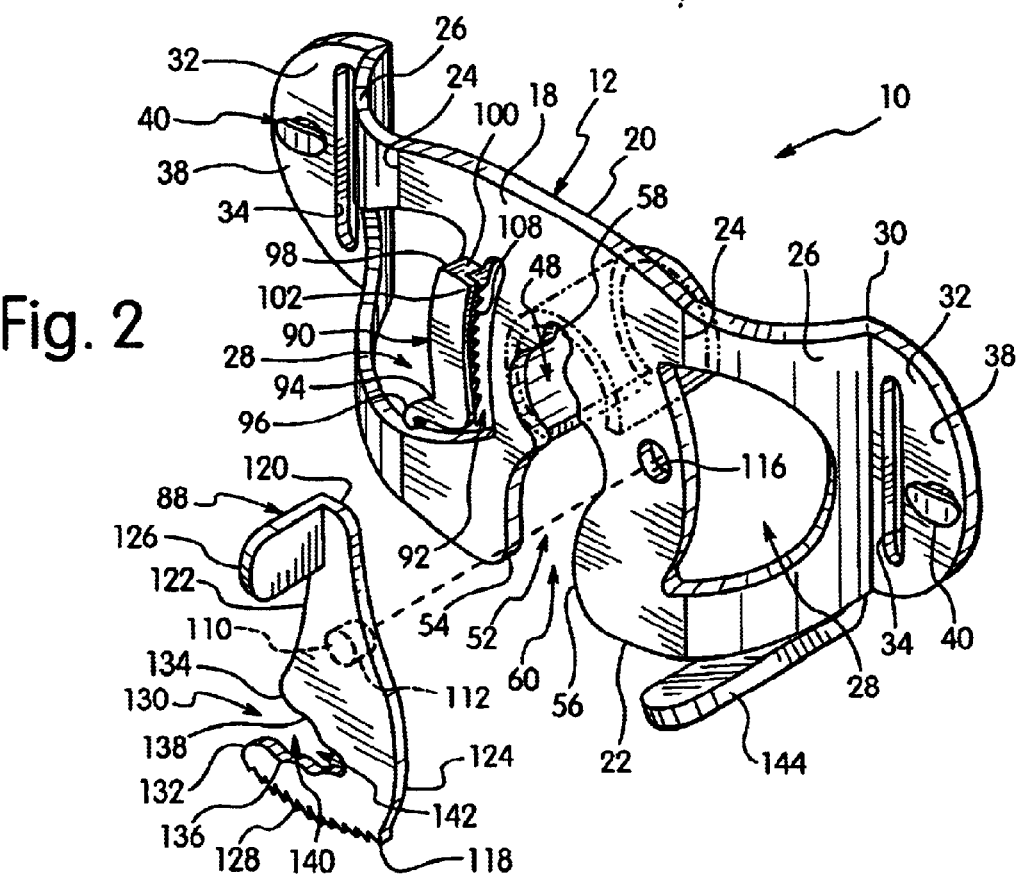
FIG. 2 is an exploded perspective view of the device of FIG. 1.
Figure 3:
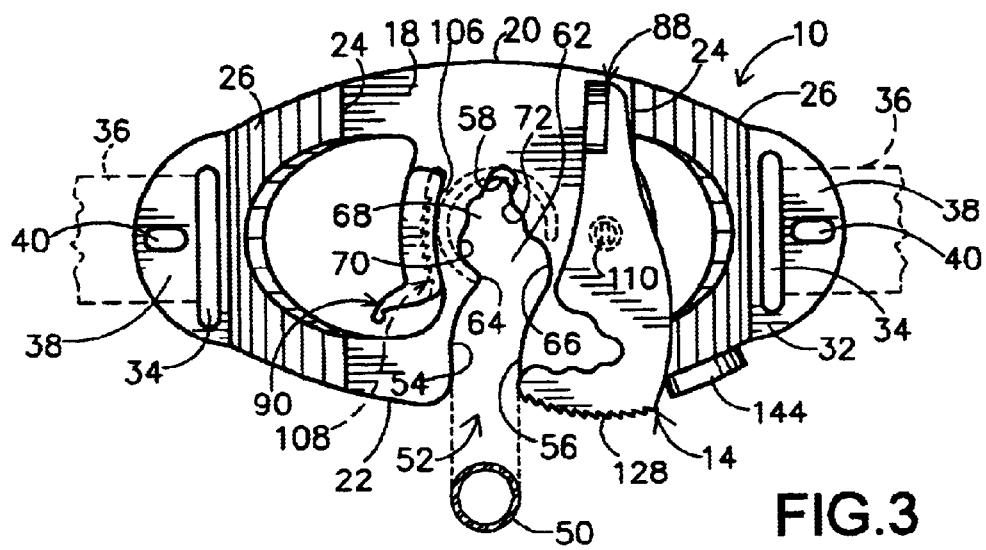
FIG. 3 is a top view of the device of FIG. 1 showing the tracheal tube aligned with the opening in the device.
Figure 5:
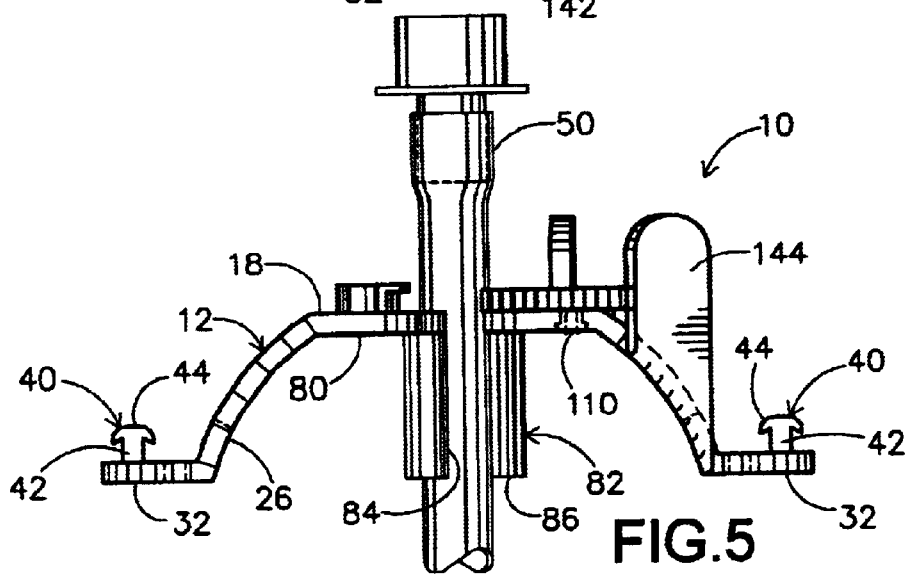
FIG. 5 is an end view of the device of FIG. 1 with the latching jaw in the open position.

As shown in FIGS. 2 and 3, arcuate legs 26 and central body portion 18 each include an opening 28 on each side of central body portion 18. Openings 28 are positioned to overlie the mouth of the patient when device 10 is in use to allow access to the patient's mouth. Arcuate legs 26 extend from central body portion 18 and terminate at an outer end 30. Coupling tabs 32 extend from outer ends 30 of each arcuate leg 26 as shown in FIG. 5. Coupling tabs 32 in the embodiment illustrated extend in a plane substantially parallel to central body portion 18. In further embodiments, coupling tabs 32 can extend in a plane away from central body portion 18 and generally continue along the curvature of arcuate legs 26.

Figure 4:
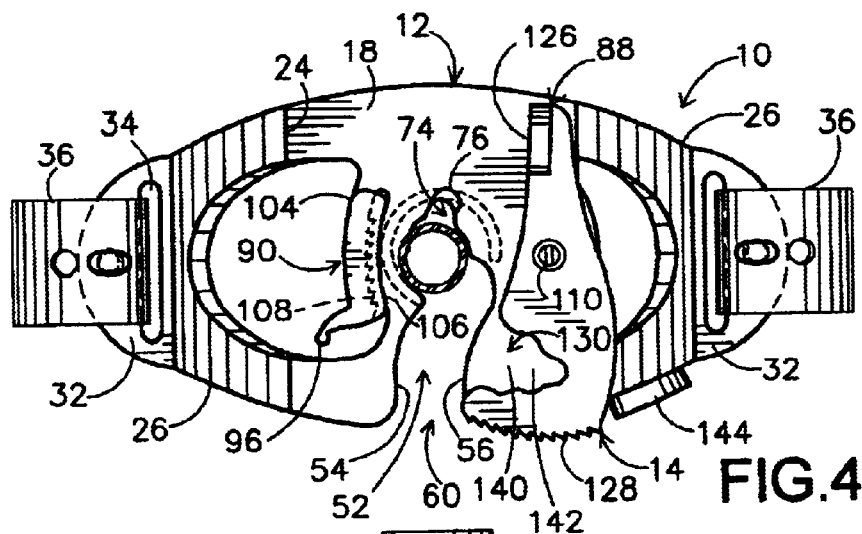
FIG. 4 is a top view of the device of FIG. 1 showing a tracheal tube positioned in the opening of the device.

Coupling tabs 32 include a slot 34 for receiving a strap 36 for attaching device 10 to the patient. Slot 34 is spaced from an outer edge 38 of each coupling tab 32 as shown in FIGS. 3 and 4. Coupling tabs 32 also include a coupling member 40 for coupling strap 36 to coupling tabs 32. Coupling member 40 in preferred embodiments includes a shaft 42 extending from coupling tab 32 in a substantially perpendicular direction to coupling tab 32. Shaft 42 includes an enlarged head 44 at its top end. Preferably, coupling member 40 is positioned between slot 34 and outer edge 38 of coupling tab 32.

Strap 36 is preferably an elastic, rubber-like material capable of securely attaching device 10 to a patient. Strap 36 includes a plurality of spaced-apart holes 46 dimensioned to receive coupling member 40. Preferably holes 46 have a dimension complementing the diameter of shaft 42 and smaller than head 44. Strap 36 extends through slot 34 and is attached to coupling member 40 by passing enlarged head 44 through a selected hole 46. The elastic properties of the strap 36 allow head 44 to pass through hole 46 and securely attach strap 36 to device 10. Holes 46 are spaced apart a distance to provide selective adjustment of the effective length of strap 36 for securely attaching device 10 to a patient. In use, strap 36 is passed around a patient's neck as shown in FIG. 1 and inserted upwardly through slot 34. The end of strap 36 is pulled upward to apply tension to the strip and then pulled downward to force coupling member through a hole 46 in strap 36. Strap 36 can be released by pulling upward on the end of the strap to pull the strap away from the coupling member.

Referring to FIGS. 2–4, second longitudinal edge 22 of central body portion 18 includes an opening 48 dimensioned to receive a tracheal tube 50. Opening 48 forms a channel extending transversely through central body portion 18. In preferred embodiments, opening 48 is formed by a slot 52 that is open to second longitudinal edge 22. In the embodiment illustrated in FIG. 3, slot 52 has a generally S-shaped configuration having side walls 54 and 56. As shown in FIGS. 2 and 3, side walls 54 and 56 converge to an end 58. Slot 52 has an open end 60 dimensioned to receive tracheal tube 50. Side walls 54 and 56 gradually converge for gripping tracheal tube 50. Slot 52 has a curved section 62 formed by a convex portion 64 of side wall 54 and a concave portion 66 of side wall 56. Slot 52 has a second open portion 68 defined by a concave surface 70 of side wall 54 and a concave portion 72 of side wall 56. Concave portions 70 and 72 form a substantially circular area for receiving tracheal tube 50 as shown in FIG. 4. As shown in FIG. 4, tracheal tube 50 snaps into the circular area defined by concave portions 70 and 72.

Side walls 54 and 56 of slot 52 converge toward end 58 to define a third open portion 74. Third open portion 74 has a width less than second open portion 68 and is dimensioned to receive a small tracheal tube substantially as shown in FIGS. 12 and 13. As shown in FIG. 12, a stop member 76 extends upwardly from central body portion 18 adjacent third open portion 74 to support a small tracheal tube 78.

Central body portion 18 includes a bottom side 80 having a channel member 82 extending therefrom. Channel member 82 surrounds second open portion 68 and third open portion 74 of slot 52. In the embodiment shown in FIG. 2 and FIG. 5, channel member 82 has a substantially semicircular shape with a longitudinal opening 84 aligned with slot 52. Longitudinal opening 84 is positioned so that channel member 82 does not block slot 52 so that a tracheal tube can slide laterally through slot 52 into channel member 82. Preferably, channel member 82 has an open axial end 86 spaced from central body portion 18. Channel member 82 has a longitudinal length sufficient to pass between the teeth of a patient and an inner diameter to receive a tracheal tube. Channel member 82 is dimensioned to substantially surround the tracheal tube to prevent the patient from biting and collapsing the tube.

Clamping assembly 14 includes a movable jaw 88 and a flexible latching arm 90. Latching arm 90 is integrally formed with central body portion 18 and is formed by a slot 92 shown in FIG. 2 extending generally concentric with second open portion 68 of slot 52. As shown in FIGS. 2 and 3, latching arm 90 includes an outer end 94 having a tab 96 extending therefrom. Latching arm 90 includes a base 98 coupled to central body portion 18 to form a living hinge. As shown in FIG. 2, latching arm 90 has a thickness greater than the thickness of central body portion 18 and extends above the plane of outer surface of center body portion 18. Latching arm 90 has a top surface 100 spaced from the surface of central body portion 18. A ledge 102 extends from top surface 100 inwardly toward slot 52. Latching arm 90 also includes an outer face 104 and an inner face. Inner face 106 forms a latching member for engaging jaw 88. The inner face has a substantially concave shape with a plurality of ratcheting teeth 108.

Jaw 88 is coupled to central body portion 18 by a pivot pin 110. In the embodiment illustrated, pivot pin 110 is integrally formed with jaw 88 and includes a shaft 112 and an enlarged head. Central body portion 18 includes an aperture 116 as shown in FIG. 1 to receive pivot pin 110 for pivotally coupling jaw 88 to central body portion 18. In this embodiment, aperture 116 and pivot pin 110 define a pivot axis spaced laterally from slot 52 in frame 12 and at a midpoint between first end 118 and second end 120 of jaw 88. As shown in the figures, slot 130 of jaw 88 is positioned between first end 118 and pivot pin 110.

As shown in FIGS. 2–4, jaw 88 has a first end 118, a second end 120, a first side edge 122, and a second side edge 124. First end 118 of jaw 88 includes a substantially arcuate shape with a plurality of ratcheting teeth 128. Second end 120 of jaw 88 has an upstanding tab 126 operating jaw 88. Teeth 128 are dimensioned to complement teeth 108 of latching arm 90. As shown in FIG. 2, teeth 128 are inclined with respect to second end 120 of jaw 88 to ratchet into engagement with teeth 108 and retaining jaw 88 in the clamping position until released by lifting tab 96 away from jaw 88.

First side edge 122 of jaw 88 includes a slot 130 having side walls 132 and 134. Side walls 132 and 134 include a first recessed portion 136 and 138, respectively, to define a first open portion 140. Side walls 132 and 134 converge to form a second recessed portion 142 having a dimension less than first open portion 140. As shown in FIG. 3, first open portion 140 has a dimension corresponding substantially to second open portion 68 of slot 52 in central body portion 18.

Figure 6:
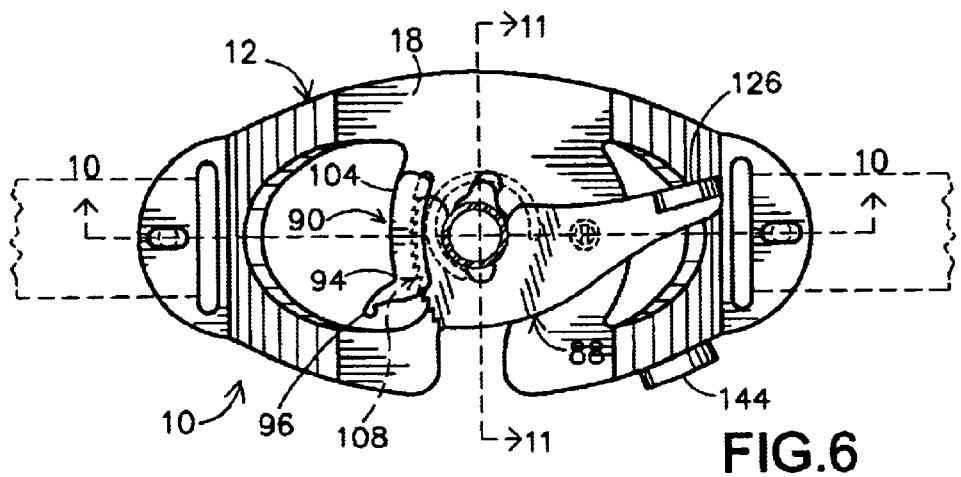
FIG. 6 is a top view of the device of FIG. 1 showing the latching jaw in the clamping position.
Figure 7:
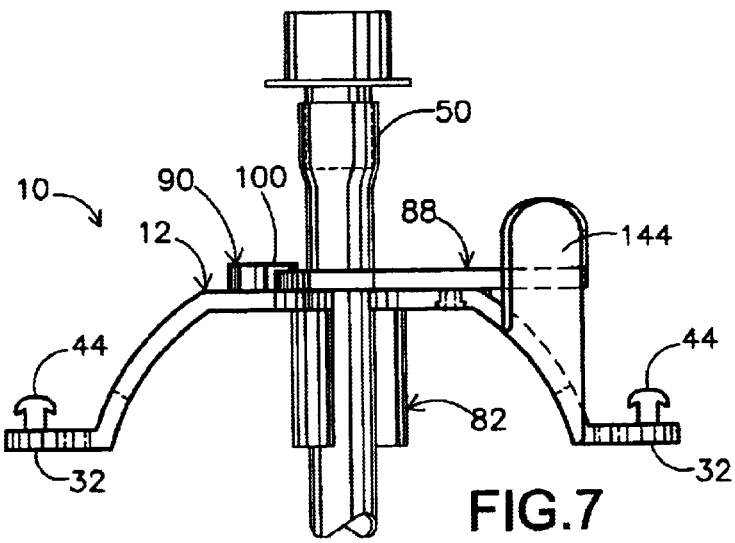
FIG. 7 is a front side view of the device of FIG. 1 showing the jaw in the clamping position.
Figures 8, 9:
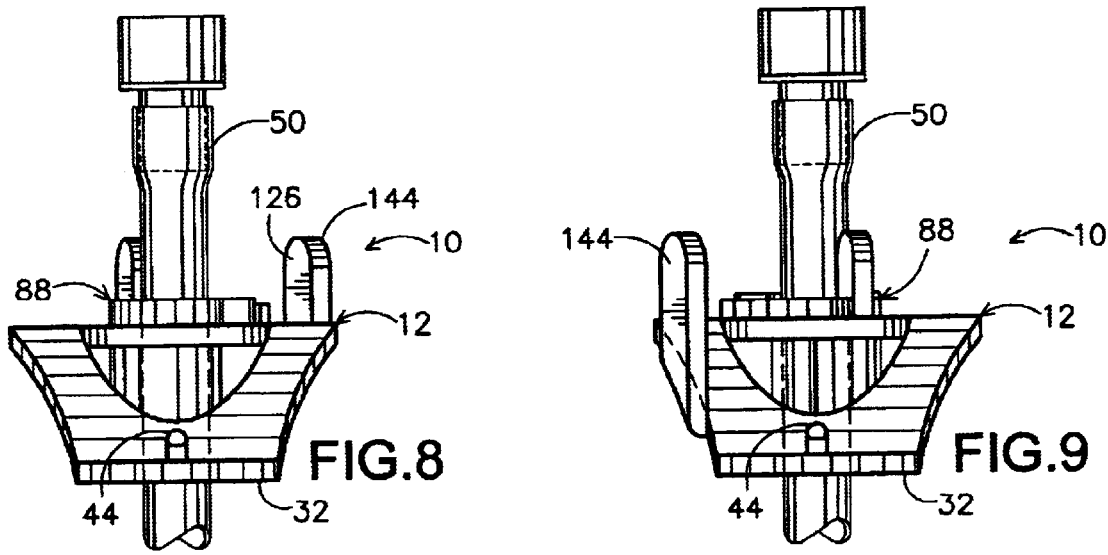
FIG. 8 is a left side view of the device of FIG. 6.
FIG. 9 is a right side view of the device of FIG. 6.

Jaw 88 is mounted on central body portion 18 for pivotal movement from an open position shown in FIG. 3 to a clamping position shown in FIG. 6. In use, a tracheal tube 50 is positioned in a patient's throat. With jaw 88 in the open position, tracheal tube 50 is then passed transversely through slot 52 through open end 60. Depending on the outer dimension of tracheal tube 50, tracheal tube 50 is positioned in either second open portion 68 or third open portion 74 of slot 52 as shown in FIG. 3 or FIG. 12. A thumb tab 144 extends from frame 12 to cooperate with tab 126 of jaw 88. Jaw 88 is then pivoted about the pivot pin 110 to close slot 52 in central body portion 18 as shown in FIG. 5. Jaw 88 is pivoted whereby teeth 128 ratchet with teeth 108 on latching arm 90 to latch jaw 88 in the closed position. Ratcheting teeth 108 and 128 are inclined to allow jaw 88 to ratchet into the latching position. Latching arm 90 can be flexed outward from central body portion 18 by pressing on tab 96 to release teeth 108 from teeth 128 of jaw 88. Jaw 88 can then be opened to remove tracheal tube 50 from frame 12.

In the illustrated embodiment of the invention, the support for device 10 is frame 12 having a dimension to substantially cover a patient's mouth. In other embodiments, frame 12 can have a smaller dimension to cover only a portion of the mouth. In this embodiment, frame 12 is positioned over the patient's mouth and secured in place by the strap. During use and the clamping operation, frame 12 is intended to be substantially stationary with respect to the patient. Pivoting jaw 88 with respect to frame 12 effective clamps tracheal rube in the slots of jaw 88 and frame 12.

In the embodiment of FIGS. 1–13, jaw 88 is pivotally coupled to frame 12 about a pivot axis extending transversely through frame 12. The pivot axis of jaw 88 is positioned between the first and second ends of jaw 88. In the illustrated embodiment, the latching members are ratchet teeth 128 on the first end of jaw 88 although other latching members can be used. Slot 130 of jaw 88 is positioned between the first end and ratchet teeth 128 and the pivot axis of jaw 88.

EMBODIMENT OF FIGS. 14 AND 15

Figure 14:
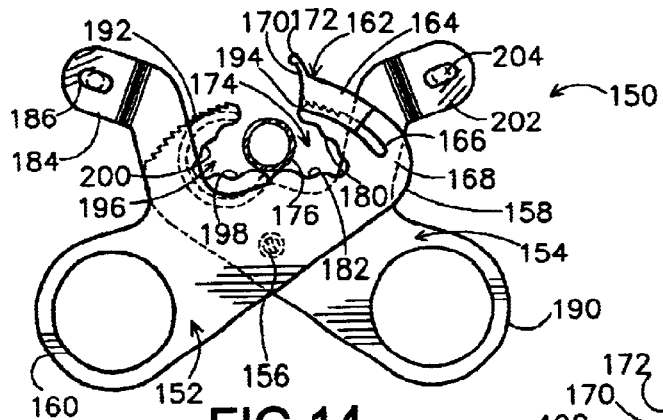
FIG. 14 is a top view of the tracheal tube holding device in a second embodiment showing the device in the open position.
Figure 15:
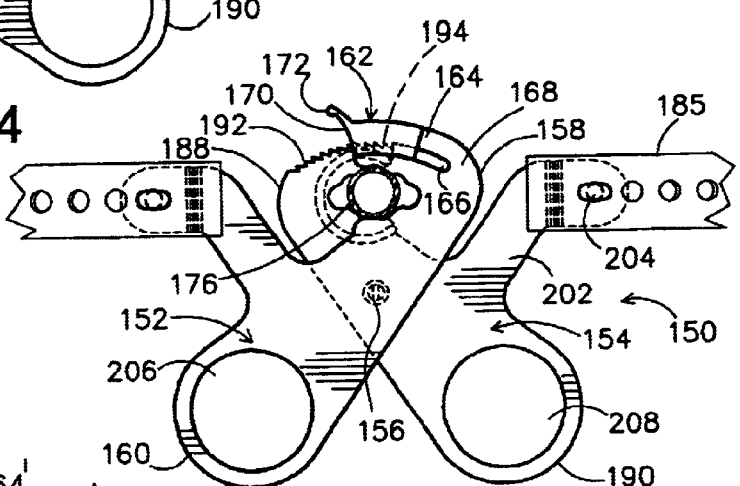
FIG. 15 is a top view of the device of FIG. 14 showing the device in the clamping position.

FIGS. 14 and 15 show a second embodiment of the tracheal tube holding device 150. Device 150 includes a support 152 and a pivotable jaw 154. As shown in FIG. 14, jaw 154 is pivotally coupled to support 152 by a pivot pin 156 defining a pivot axis.

Support 152 includes a first end 158 and a second end 160. Pivot pin 156 extends through support 152 at a point between first end 158 and second end 160. First end 158 of support 152 has a first latching member 162. Latching member 162 is formed by a flexible arm 164 defined by a slot 166. Arm 164 has a base 168 integrally formed with first end 158 to allow a flexing movement of arm 164 in the plane of support 152. Arm 164 includes an outer end 170 having a tab 172 for manually flexing arm 164 away from support 152.

Support 152 includes a recess 174 for receiving a tracheal tube 176. Recess 174 is an open slot that opens in a transverse direction with respect the longitudinal dimension of support 152. Recess 174 has side edges with first concave portions 178 and a second concave portion 180. As in the previous embodiment, side edges of recess 174 converge to a bottom end 182 for gripping tracheal tube 176.

A coupling tab 184 extends from support 152 along a transverse side edge. In the embodiment illustrated, coupling tab 184 is positioned between the pivotal axis defined by pivot pin 156 and second end 160 of support 152. A coupling member 186 is formed on coupling tab 184 for attaching to a strap 185 as in the previous embodiment for securing device 150 to a patient.

Movable jaw 154 has a longitudinal dimension with a first end 188 and a second end 190. In a preferred embodiment, pivot pin 156 is integrally formed with jaw 154 and extends transversely from the face of jaw 154. Preferably, pivot pin 156 is positioned between first end 188 and second end 190. First end 188 of jaw 154 has an arcuate face with ratcheting teeth 192. Ratcheting teeth 192 are dimensioned to cooperate with ratcheting teeth 194 on the inner surface of arm 164.

Jaw 154 includes a recess 196 having a shape that is substantially a mirror image of recess 174. Recess 176 includes converging side walls having a first concave portion 198 and a second concave portion 200.

A coupling tab 202 extends from jaw 154 from a position between pivot pin 156 and second end 190 of jaw 154. Coupling tab 202 is substantially a mirror image of coupling tab 184 and includes a coupling member 204 for attaching to strap 185.

In use, device 150 is placed over the mouth of a patient in the open position shown in FIG. 14 and secured by extending the strap around the patient's neck. Tracheal tube 176 is placed between support 152 and jaw 154 in recess 174 and 196, respectively, as shown in FIG. 14. Jaw 154 is then pivoted about pivot pin 156 with respect to support 152 to clamp tracheal tube 176 within recesses 174 and 196 as shown in FIG. 15. Ratcheting teeth of jaw 154 engage teeth 194 of arm 164 to retain device 150 in the clamped position.

Preferably, the second end 160 of support 152 and second end 190 of jaw 154 include an actuating member to assist in pivoting jaw 154 with respect to support 152. In the embodiment illustrated, the actuating member is a finger hole 206 and 208 in support 152 and jaw 154, respectively. Alternatively, the actuating members can be a tab or other actuator member.

EMBODIMENT OF FIGS. 16 AND 17

Figure 16:
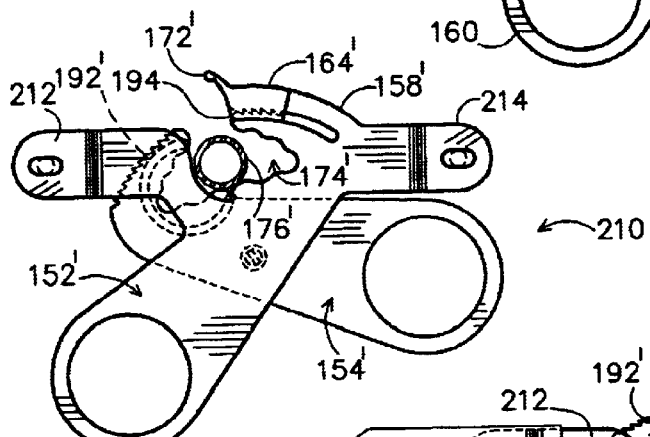
FIG. 16 is a top view of the tracheal tube holding device in a third embodiment showing the device in the open position.
Figure 17:
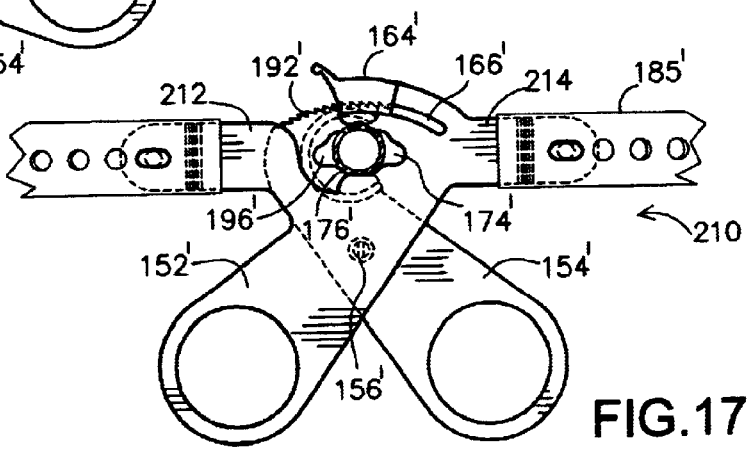
FIG. 17 is a top view of the device of FIG. 16 showing the device in the clamping position.

Referring to FIGS. 16 and 17, a third embodiment of a tracheal tube holding device 210 is illustrated. Device 210 is similar to device 150 except for the position of coupling tabs 212 and 214. Accordingly, identical components are identified by the same reference number with the addition of a prime.

As shown in FIG. 16, support 152' includes coupling tab 212 extending from a side edge substantially at the pivot axis defined by pivot pin 156'. The second coupling tab 214 is also coupled to support 152' at first end 158'. As shown in FIG. 16, coupling tabs 212 and 214 are fixed to support 152' and extend in opposite directions from recess 174' of support 152'. In preferred embodiments, coupling tabs 212 and 214 are aligned with recess 174' and extend along a common axis.

In use, support 152' is positioned over the patient's mouth and secured by the strap extending around the patient's neck. A tracheal tube 176' is positioned in recess 174' of support 152'. Jaw 154' is then pivoted about pivot pin 156' to clamp tracheal tube 176' in recesses 174 and 196. Ratcheting teeth 192' of jaw 154' engage teeth 194' of movable arm 164'. As in the previous embodiments, arm 164' can be flexed away from support 152' to release ratcheting teeth 192' to open jaw 154'.

EMBODIMENT OF FIGS. 18 AND 19

Figure 18:
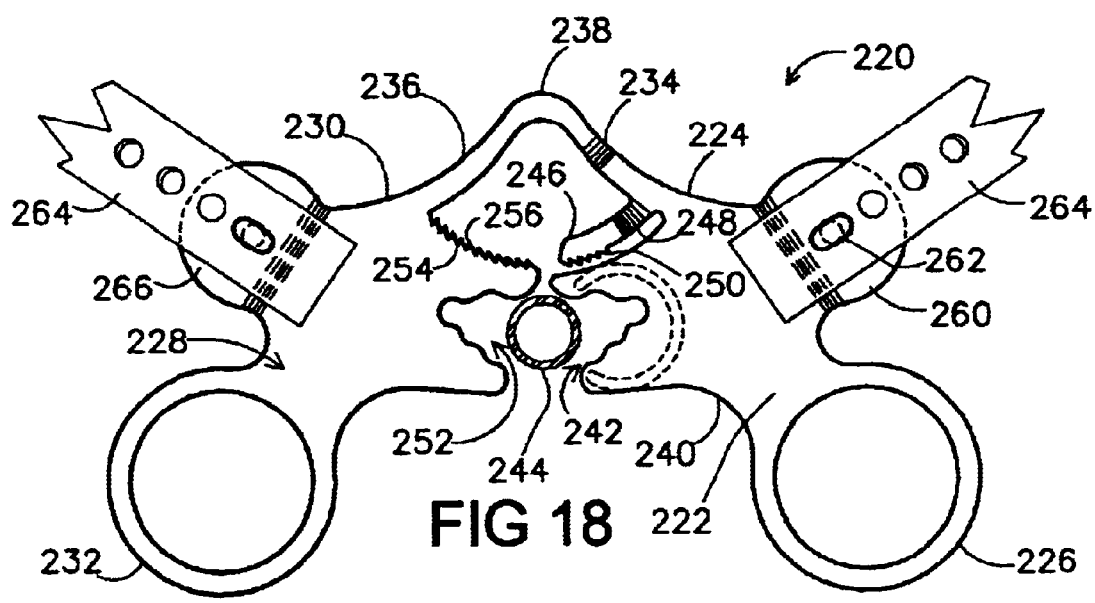
FIG. 18 is a top view of the tracheal tube holding device in a fourth embodiment showing the device in the open position.
Figure 19:
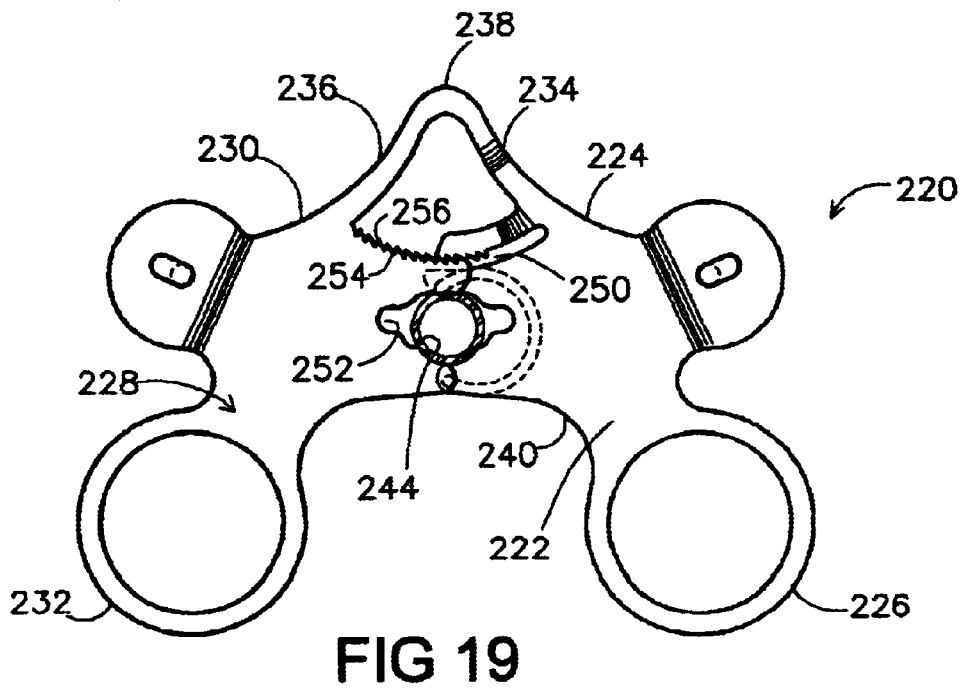
FIG. 19 is a top view of the device of FIG. 18 showing the device in the clamping position.

FIGS. 18 and 19 show a fourth embodiment of the tracheal tube holding device 220. Device 220 includes a support 222 having a first end 224 and a second end 226. Device 220 also includes a movable jaw 228 having a first end 230 and a second end 232. A flexible arm 234 extends outwardly from first end 224 of support 222. Movable jaw 228 has a flexible arm 236 extending from first end 230. Arm 234 is integrally formed with arm 236 at a point 238 to define a flexible living hinge for pivoting jaw 228 with respect to support 222.

Support 222 has a first side 240 having a slot or recess 242 for receiving a tracheal tube 244. Slot 242 is substantially the same as the slots in the previous embodiments. Support 222 includes a flexible arm 246 having an arcuate face 248 with ratcheting teeth 250. Support 228 includes a slot 252 complementing slot 242 for clamping tracheal tube 244. Jaw 228 includes an arcuate face 254 having ratcheting teeth 256 for engaging teeth 250 of arm 246.

A first coupling tab 260 extends outwardly from a second side 262 of support 222 for coupling to a strap 264. A second coupling tab 266 extends from support 228 for coupling to strap 264.

In use, device 220 is positioned over the mouth of a patient and secured by strap 264. A tracheal tube 244 is positioned between support 222 and jaw 228. Jaw 228 is then pivoted about the hinge 238 toward support 222 to clamp tracheal tube 244 in slots 242 and 252 as shown in FIG. 19. As in the previous embodiments, the ratcheting teeth 256 and 250 form a latching assembly to latch device 220 in the clamping position. Flexible arm 248 can be flexed outwardly to release teeth to open device 220.

While various embodiments have been chosen to illustrate the invention, it will be understood by those skilled in the art that various additions and modifications can be made without departing from the scope of the invention as defined in the appended claims.

What is claimed is:

1. A tracheal tube holding device for stabilizing a tracheal tube in the mouth of a patient, said device comprising:
   a frame dimensioned to fit over a patient's mouth and having an open slot extending transversely through said frame and being dimensioned to receive a tracheal tube, said slot having two side walls, each side wall having a first recess therein forming a first open portion for receiving a first tracheal tube having a first diameter;
   a jaw pivotally coupled to said frame and being pivotable about a pivot axis on said frame between an open position to a clamping position to clamp a tube in said opening of said frame; and
   a releasable latching assembly for latching said jaw in said clamping position.

2. The device of claim 1, wherein said jaw is coupled to said frame by a coupling pin, and wherein said jaw is pivotable about said pin.

3. The device of claim 1, wherein said jaw has a first end and a second end, said pivot axis being positioned between said first and second ends of said jaw, said first end of said jaw facing radially outward from said pivot axis and being movable in an arcuate path about said pivot axis between said open position to said clamping position.

4. The device of claim 3, wherein said jaw includes a first side extending in a substantially radial direction with respect to said pivot axis.

5. The device of claim 4, wherein said first side of said jaw includes a recess cooperating with said opening in said frame for clamping said tracheal tube when said jaw is in said clamping position.

6. The device of claim 5, wherein said recess in said jaw is located between said pivot axis and said first end.

7. The device of claim 5, wherein said frame includes a first end, a second end, a first side, and a second side, said slot being formed in said first side.

8. The device of claim 4, wherein said jaw includes a second end spaced from said first end and having an operating arm for moving said jaw.

9. The device of claim 3, wherein said latch assembly comprises a first latch member on said first end of said jaw and a second latch member on said frame for latching with said first latch member.

10. The device of claim 9, wherein said second latch member comprises a flexible arm coupled to said frame, said flexible arm being cantilevered with respect to said frame and being flexible in a plane of said frame.

11. The device of claim 10, wherein said second latch member comprises a plurality of ratcheting teeth.

12. The device of claim 11, wherein said first latch member comprises a plurality of ratcheting teeth cooperating with said ratcheting teeth of said first latch member.

13. The device of claim 1, wherein said side walls of said slot in said frame each have a second recess therein forming a second open portion for receiving a tracheal tube of a second diameter, wherein said first open portion is larger than said second open portion.

14. A tracheal tube holding device for stabilizing a tracheal tube in the mouth of a patient, said device comprising:
   a support dimensioned to fit over a patient's mouth, said support having a first end, a second end, first and second sides extending between said first and second ends, a front face and a rear face, said first side having an open slot defining an opening extending transversely through said support for receiving a tracheal tube, said slot having a bottom end;
   a guide member coupled to said rear face of said support and surrounding said bottom end of said slot for guiding a tracheal tube to said patient;
   a jaw pivotally coupled to said support by a coupling pin, said jaw having a side with a slot therein complementing said slot of said support, said jaw being pivotable between an open position and a clamping position to clamp a tracheal tube in said slot in said support and said slot in said jaw; and
   a releasable latching assembly for latching said jaw in said clamping position.

15. The device of claim 14, wherein said coupling pin extends from said jaw and is received in an aperture in said support.

16. The device of claim 14, where said slot in said support has a first open portion for receiving a first tracheal tube having a first diameter and a second open portion for receiving a tracheal tube of second diameter, wherein said first portion is larger than said second portion.

17. The device of claim 16, where said slot in said jaw has a open first portion for receiving said first tracheal tube and has a second open portion for receiving said tracheal tube.

18. The device of claim 14, wherein said jaw has a first end facing radially outward from a pivot axis and a first side extending between said first end and said pivot axis, said first side of said jaw being movable in an arcuate path about said pivot axis between said open position to said clamping position.

19. The device of claim 18, wherein said latching assembly includes a first latch member on said first end face of said jaw.

20. The device of claim 19, wherein said latching assembly includes a second latching member on said support for latching with said first latch member.

21. The device of claim 20, wherein said first and second latch members comprise a plurality of ratcheting teeth.

22. The device of claim 18, wherein said first latching member is a flexible arm coupled to said support cooperating with said jaw.

23. The device of claim 14, wherein said guide member has a substantially C-shape having an axial passage dimensioned to receive said tracheal tube.

24. A tracheal tube holding device for holding a tracheal tube in the mouth of patient, comprising:
   a support dimensioned to fit over a patient's mouth, said support having a first end, a second end, a first side, a second side, said first side having a recess defining an opening extending transversely through said support for receiving a tracheal tube, said opening being located between said first and second ends;
   a jaw coupled to said support and being pivotable about a pivot axis, said jaw being pivotable between an open position and a clamping position, said jaw having a first end with a first latching member and having a recess for cooperating with said recess in said support; and
   a second latching member coupled to said first end of said support having a side edge facing said opening in said support and positioned to engage said first latching member of said jaw for latching said jaw in said clamping position, said second latching member comprising a flexible latching arm coupled to said support for releasably coupling with said first latching member, said flexible latching arm having a first end fixed to said support and a second free end, and being flexible about said first end whereby said second end is movable in a direction away from said jaw to release said jaw from said clamping position.

25. The device of claim 23, wherein said jaw is coupled to said support by a pivot pin defining a pivot axis of said jaw extending through said support, said pivot axis being located between said opening and said second end of said support, and wherein said first end of said jaw moves in an arcuate path about said pivot axis between said open position and said clamping position.

26. The device of claim 24, wherein said first latching member comprises a plurality of ratcheting teeth.

27. The device of claim 26, wherein said flexible latching arm comprises a plurality of ratcheting teeth positioned for engaging said first ratcheting teeth.

28. A tracheal tube holding device for holding a tracheal tube in the mouth of patient, comprising:

a support dimensioned to fit over a patient's mouth, said support having a first end, a second end and an opening extending transversely through said support for receiving a tracheal tube, said opening being located between said first and second ends;

a jaw coupled to said support and being pivotable about a pivot axis, said jaw being pivotable between an open position and a clamping position, said jaw having a first end with a first latching member; and a second latching member coupled to said first end of said support and positioned to engage said first latching member of said jaw for latching said jaw in said clamping position, said second end of said support including a first actuator member, and said jaw having a second end with a second actuator member, said first and second actuator members being positioned for pivoting said jaw between said open position and said clamping position.

29. The device of claim 28, wherein said first and second actuating members have a finger opening dimensioned to receive a finger of an operator.

30. The device of claim 28, wherein said first end of said support includes a first coupling member, and said first end of said jaw includes a second coupling member, and a strap coupled to said first and second coupling members for encircling the neck of a patient.

31. A tracheal tube holding device for holding a tracheal tube in the mouth of patient, comprising:

a support dimensioned to fit over a patient's mouth, said support having a first end, a second end and an opening extending transversely through said support for receiving a tracheal tube, said opening being located between said first and second ends;

a jaw coupled to said support and being pivotable about a pivot axis, said jaw being pivotable between an open position to a clamping position, said jaw having a first end with a first latching member;

a second latching member coupled to said first end of said support and positioned to engage said first latching member of said jaw for latching said jaw in said clamping position; and a first flexible leg coupled to said first end of said support, and a second flexible leg coupled to said first end of said jaw, said first and second legs being coupled together to define said pivot axis.

32. A tracheal tube holding device for holding a tracheal tube in the mouth of patient, comprising:

a support dimensioned to fit over a patient's mouth, said support having a first end, a second end and an open slot extending transversely through said support for receiving a tracheal tube, said open slot being located between said first and second ends and having a depth greater than a width of the tracheal tube, whereby said tracheal tube is received completely in said slot;

a jaw coupled to said support and being pivotable about a pivot axis, said jaw being pivotable between an open position and a clamping position, said jaw having a first end and a second end with said pivot axis being positioned between said first end and a second end, a side edge extending between said first end and said second end, said first end defining a first latching member; and a flexible arm having a second latching member and being coupled to said support and positioned to engage said first latching member of said jaw for latching said jaw in said clamping position, said flexible arm being oriented in a plane parallel to and spaced from a plane of said support, and having a first end fixed to said support and a second free end, said flexible arm being sufficiently resilient to bend away from said jaw between a latching position and an unlatching position with respect to said jaw.

33. The device of claim 32, wherein said flexible arm is resiliently flexible in said plane parallel to a plane of said support.

34. The device of claim 33, wherein said first latching member on said jaw comprises a plurality of ratcheting teeth, and wherein said flexible arm includes a plurality of ratcheting teeth for mating with said ratcheting teeth on said jaw.

35. The device of claim 33, wherein said flexible arm has a longitudinal side edge facing said open slot.

36. The device of claim 35, wherein said longitudinal side edge includes said second latching member.

37. The device of claim 32, wherein said first end of said jaw has a substantially arcuate shape and a plurality of first ratchet teeth on said first end, and where said flexible arm has a substantially arcuate shape with a plurality of second ratchet teeth for cooperating with said first ratchet teeth on said jaw.

* * * * *